United States Patent [19]

Hoogendoorn et al.

[11] 4,150,113

[45] Apr. 17, 1979

[54] ENZYMATIC DENTIFRICES

[75] Inventors: Hendrik Hoogendoorn, Krimpen aan den Ijssel; Rutger Matthijsen; Huibert C. T. Moelker, both of Oss, all of Netherlands

[73] Assignee: Telec S.A., Switzerland

[21] Appl. No.: 870,815

[22] Filed: Jan. 19, 1978

Related U.S. Application Data

[63] Continuation of Ser. No. 651,862, Jan. 23, 1976, abandoned, which is a continuation-in-part of Ser. No. 349,377, Apr. 9, 1973, abandoned, which is a continuation-in-part of Ser. No. 276,390, Jul. 21, 1972, abandoned, which is a continuation-in-part of Ser. No. 39,887, May 22, 1970, abandoned.

[30] Foreign Application Priority Data

Jun. 3, 1969 [NL] Netherlands ............... 6908379

[51] Int. Cl.² .................................................. A61K 7/28
[52] U.S. Cl. ............................................ 424/50; 424/48
[58] Field of Search ........................................ 424/50, 48

[56] References Cited

U.S. PATENT DOCUMENTS

| | | | |
|---|---|---|---|
| 1,171,392 | 2/1916 | Meier | 426/3 |
| 2,198,865 | 4/1940 | Dyckman | 426/3 |
| 2,218,172 | 10/1940 | Kokatnur | 424/48 |
| 2,290,862 | 7/1942 | Canning | 426/3 |
| 2,891,868 | 6/1959 | Heggie et al. | 426/10 |
| 3,095,307 | 6/1963 | Scott et al. | 426/10 |
| 3,160,508 | 12/1964 | Scott | 426/10 |
| 3,193,393 | 7/1965 | Scott | 426/10 |
| 3,194,738 | 7/1965 | Harrison et al. | 426/3 |
| 3,574,824 | 4/1971 | Echlanna et al. | 424/50 |
| 3,686,393 | 8/1972 | Woodruff et al. | 424/50 |

FOREIGN PATENT DOCUMENTS 2027019 12/1970 Fed. Rep. of Germany.
7003487 11/1970 South Africa.

OTHER PUBLICATIONS

C.A. 37, #1467(4), #2036(8), #3789(3), #4421(1)(1943) 38, #137(6)(1944) 39, #5261(1)(1945).
C.A. 40, #6546(6)(1946) 41, #2165C(1947) 42, #4636A, #4625D(1948) 43, #3857¹(1949) 44, #4055¹(1950).
C.A. 32, #721(2)(1938), 44 #6573i(1950).
Fitzgerald et al., Antibiotics & Chemotherapy 3(3):231–240, Mar. 1953, The In Vitro Effects of Antibiotics and Other Inhibitory Agents on Representive Oral Lactobacillii.
Volker et al., Antibiotics & Chemotherapy 6:56–62(1956), The Influence of Certain Protein Adsorbed Agents on Hamster Caries.
Welch et al., Antibiotics & Chemotherapy 2:249–254(1952), The Effect of Prolonged Use of Penicillin Toothpowder.

*Primary Examiner*—Shep K. Rose
*Attorney, Agent, or Firm*—Stevens, Davis, Miller & Mosher

[57] ABSTRACT

A novel enzymatic dentifrice comprises as its essential active ingredient an amount of glucose oxidane enzyme which forms hydrogen peroxide by oxidative decomposition of a glucose substrate provided by glucose present in saliva and tooth plaque so as to cause a substantial shift toward neutral values in the pH at the surface of teeth, when said pH is below the neutral range.

7 Claims, No Drawings

ENZYMATIC DENTIFRICES

CROSS-REFERENCE TO RELATED APPLICATION

This is a continuation of application Ser. No. 651,862 filed Jan. 23, 1976 now abandoned, which in turn is a continuation-in-part of Ser. No. 349,317 filed Apr. 9, 1973, now abandoned, in turn a continuation-in-part of Ser. No. 276,390 filed July 21, 1972, now abandoned, in turn a continuation-in-part of Ser. No. 39,887, filed May 22, 1970, now abandoned.

BACKGROUND OF THE INVENTION

The invention relates to a novel dentifrice containing glucose oxidase as its essential active ingredient. This enzyme is known as an oxidoreductase, and one of its characteristics is that it forms hydrogen peroxide by oxidative decomposition of its substrate glucose. The action of this enzyme in the dentifrice is twofold: (1) the formation of hydrogen peroxide tends to normalize mouth flora, thus minimizing the generation of acids with concommitant lowering of the pH at the tooth surfaces, and (2) it facilitates the loosening and removal of plaque on the teeth.

Dental caries, or tooth decay, is attributable to several factors. It is well known that as a rule there accumulates on the surface of the teeth a deposit known as plaque, which consists of micro-organisms, proteinaceous and carbohydrate substances, epithelial cells, and food debris. Plaque may be a precursor of calculus, a hard deposit which must be removed mechanically. Plaque may also possibly contribute to various pathological conditions of teeth and to soft tissue in the mouth. The bacteria present in the plaque cause the food products to decay, during which process acids are formed, lowering the pH. Many compounds have been proposed in the patent and other literature for inclusion in dentifrices or mouthwashes to inhibit the formation of plaque or to remove them once formed. Among such compounds are various organic polyphosphonates, p-aminobenzoic acid, benzohydroxamic acid, glutaraldehyde, glyoxylic acid, and many others. None of these appear to have been dependably effective.

As far as pH is concerned, at the surface of the tooth the pH of the saliva is normally about 7.0 to 7.5. Upon the consumption of certain types of foods, particularly those containing sugar, generation of acid takes place, with lowering of the pH down to 5.5 to 4.5, or even lower, a region which is regarded as contributing to tooth decay because under such acid conditions the calcium compounds of the teeth will dissolve in the acid saliva. The time required for restoration of normal pH is a factor of considerable importance, and the more acid the condition of the mouth, the longer this restoration or regeneration period becomes. Dependent upon the nature of the food consumed and the frequency of consumption, the pH can reach varying values, while the time required for the restoration of the normal pH (regeneration time) can also vary greatly. Thus, for example, it has been found that during the consumption of sugars in the form of tough masses, such as toffees, a much lower pH is reached than when these sugars occur in a product with a fibrous structure such as apples, the regeneration time in the first case being moreover much longer.

Further, it has been found that in the repeated consumption of sweets or other products forming acids, the regeneration time gradually increases. Dependent upon the nature of the material the pH can reach values of from 5.5 to 4.5 and sometimes even lower. The zone below the limit of pH about 5.5 is often called the danger zone because under such acid conditions the calcium compounds of the tooth will dissolve in the saliva leading to decay of the tooth. Consequently it will be clear that the lower the pH is and the longer the regeneration time, the greater will be the risk of the teeth being affected.

Besides these two factors there is at least one other factor which plays an important part in tooth decay, i.e. the thickness of the plaque. The fact of the matter is that if the plaque is very thick the acids formed in it by bacterial decomposition have great difficulty in diffusing to the surface, resulting in a lower pH and a longer regeneration period.

In connection with the last-mentioned factor it has been conventional for a considerable time past to incorporate abrasive and/or polishing material in toothpastes for the purpose of removing or reducing the plaque, which is the reason why the eating of apples is recommended.

Enzymes are commonly classified according to their mode of action, e.g. hydrolysis, oxidation, or reduction. The hydrolytic enzymes are known as hydrolases, that is, they bring about decomposition of a substrate by the incorporation of water.

It is also known to incorporate enzymes in toothpastes and similar dentifrices, e.g. proteases, such as pepsin, pancreatin, trypsin and the like, or amylases. All the enzymes that have been applied so far belong to the group of hydrolases, namely the enzymes which are, among other things, capable of breaking peptide or glycoside bonds in consequence of which macromolecular compounds are converted into oligomer or monomer products which dissolve more easily in saliva and can thus be removed.

SUMMARY OF THE INVENTION

In accordance with the present invention, there is incorporated in a dentifrice a particular enzyme, which as far as known, has not been utilized for this purpose, and the use of which is based on an entirely different and novel principle. The enzyme employed in a dentrifice in accordance with the invention is glucose oxidase. This enzyme forms hydrogen peroxide by oxidative decomposition of its substrate glucose. This glucose substrate is usually already present in the plaque and saliva in sufficient amount, and hence does not have to be added to the dentifrice, in general.

By employing this oxidoreductase enzyme as an active ingredient of a dentifrice, there is imparted to the dentifrice an entirely novel principle of action as far as the milieu of the teeth and mouth is concerned, with remarkably beneficial results. The most significant result is the formation of hydrogen peroxide by enzymatic decomposition in situ which has been found to normalize the mouth flora, in consequence of which there is a decrease in bacterial decomposition, and, consequently, an inhibition or minimization of the formation of harmful acids, which is evidenced by a significant increase in the pH at the dental surfaces. A second and very desirable result is that the structure of the plaque is rendered less firm, so that its ease of removal is greatly increased. The resulting dentifrices exhibit excellent anti-caries activity.

It has been long known that hydrogen peroxide has a bactericidal effect, and this led many years ago to proposals to incorporate in dental preparations hydrogen peroxide or mixtures yielding hydrogen peroxide. However, such preparations do not affect the plaque, nor do they inactivate the acid-forming bacteria in the plaque. Their usefulness is mainly limited to possible mouth infections, and they tend to be skin-irritating, particularly in the hydrogen peroxide concentrations which they contain. Thus, Queissner U.S. Pat. No. 959,605 (1910) suggests employing in tooth-paste a solution of hydrogen peroxide held on a gypsum base by a vegetable gum, such as agar or tragacanth; the solution may contain as much as 30% $H_2O_2$ in the free state. Grueter et al., U.S. Pat. No. 975,354 (1910) discloses a dental soap which contains sodium perborate and sodium bitartrate, to which an acid salt is added to generate hydrogen peroxide. Westlake U.S. Pat. No. 975,814 (1910) is concerned with an effervescent tablet containing free hydrogen peroxide, which causes a temporary acid reaction in the mouth, which is an undesirable effect.

The peroxide-containing dentifrices of the prior art were marketed only a short time and then withdrawn, not only because of their ineffectiveness, but because they can be skin-irritating.

The reason for the inactivity of the known dental preparations toward the noxious bacteria in the plaque appears to be that hydrogen peroxide as such cannot inactivate these bacteria, but needs the enzyme lactoperoxidase, which is always present in the mouth as a component of saliva, as an oxygen carrier from peroxide to bacterium cell. If hydrogen peroxide is present in high or moderate concentrations it inhibits the lactoperoxidase, as a result of which no oxygen transfer takes place to the bacterium cell. Only in very low concentrations ($10^{-4}$% and lower) is the lactoperoxidase not inhibited, and thus by providing that hydrogen peroxide is formed mainly and continuously at this low concentration, the inactivation of the plaque bacteria is accomplished.

Thus, in accordance with the present invention, the hydrogen peroxide is not originally present, as in the preparations of the prior art but is formed in situ by the oxidoreducatase enzyme, glucose oxidase which affects the plaque on the teeth in such manner that hydrogen peroxide is released acting upon the acid-forming bacteria occurring in the plaque and on the tooth surfaces. This release at the site where the bacteria are present which gives rise to dental caries helps to retard tooth decay.

The dentifrices of the present invention containing glucose oxidase or a glucose oxidase-carbohydrase combination meet these conditions in contrast with known peroxide dentifrices as demonstrated by experimental data in Table II below.

While not wishing to be bound by any particular theory it is believed that the mode of action of the dentifrice of the invention is as follows:

As explained previously, the pH of the saliva is normally about 7.0. In the mouth, and particularly in the plaque, bacteria are present which break down food products particularly those containing sugars, by means of processes influenced and regulated by enzymes present in the bacteria. These enzymes systems causing glycolysis have as essential moieties, SH-groups. As soon as suitable food products are available glycolysis occurs with the formation of acids resulting in the lowering of the pH down to 5.5 to 4.5 or even lower. After a certain time the pH is restored to normal values. The length of this regeneration period depends upon a number of factors including the nature of the food, the frequency of consumption, and the acidity of the mouth.

If an enzymatic dentifrice is used containing glucose oxidase the glucose, already present in the plaque and saliva, is broken down and hydrogen peroxide is formed. By means of the enzyme lactoperoxidase, being present in the mouth as a component of saliva, oxygen is transferred from the hydrogen peroxide formed to the bacterium cell resulting in the oxidation of the SH-containing enzymes, which are essential for glycolysis, into inactive disulfide enzymes. Empirically it has been proven that this inactivation takes place in the period the toothpaste or another form of dentifrice is normally in contact with the teeth, i.e. 15 to 60 seconds. Even if there is no further enzymatic treatment with glucose oxidase the inactivation is maintained for at least 10 hours which means that if in this period food is taken no glycolysis occurs and the pH is maintained at about the normal value.

That the inactivation period by one treatment lasts at least 10 hours appears clearly from the results given in Table I, on page 9 of the specification. On the first day the children rinsed their mouths with an enzyme solution according to the invention (6 U glucose oxidase and 6 U glucose oxidase + 30 U amylo glucosidase). On the 2nd day they rinsed their mouths with a saccharose solution.

The number of children in the control groups having a pH lower than 5.6 amounted to 23, whereas these numbers were 9 and 0 respectively for the groups using glucose oxidase and glucose oxidase/amylo glucosidase respectively. In an additional test a number of subjects (10 in each group) in the age 18-25 years, brushed their teeth during one week with a toothpaste without enzymes (control groups) and with a toothpaste according to the invention with different amounts of enzymes. 2 × 24 hours before the pH-measurements brushing was completely stopped in every group. Thereafter the pH was measured, the mouth was rinsed during one minute with a 50% saccharose-solution, and after 10 minutes the pH was measured again.

The composition of the toothpaste was:

| | |
|---|---|
| Glycerol | 17.4% |
| Stearyl alcohol | 3.07% |
| Na-benzoate | 0.08% |
| Na-fluoride | 0.22% |
| Carraghemate | 1.8% |
| Aluminum hydroxide | 32.5% |
| Sident 20 | 1.5% |
| K-thiocyanate | 0.02% |
| Aromatic substance | 0.8% |
| Glucose oxidase | (see table) |
| Amylo glucosidase | (see table) |
| Water | ad 100% |

The results were as follows:

| Toothpaste | Glucose oxidase | Amylo glucosidase | p-H for rinsing | pH after rinsing | Drop in pH |
|---|---|---|---|---|---|
| Control | 0 | 0 | 6.8 | 5.4 | 1.4 |
| I | 1.6 U | 5 U | 7.0 | 6.5 | 0.5 |
| II | 1.8 U | 0 | 7.3 | 6.7 | 0.6 |
| III | 1.6 U | 5 U | 7.0 | 6.5 | 0.5 |
| IV | 1.6 U | 0 | 7.0 | 6.4 | 0.6 |

From the above table is appears that even 2 × 24 hours after the last treatment with an enzymatic dentifrice according to the invention the effect on the pH is significant in comparison with the control group.

DETAILED DESCRIPTION OF THE INVENTION

The quantity of the aforementioned enzyme to be used can vary considerably, but it will usually be between about 0.5 and about 20 units per gram/milliliter of the dentifrice. By one unit of enzyme is meant that quantity of enzyme which will oxidize 1 micromol of substrate per minute at 30° C. and pH 6 under standard conditions.

It has proved to be advantageous to add to the glucose oxidase containing dentifrice one or more carbohydrases which can supply glucose as substrate for the glucose oxidase applied. The carbohydrase can be, for example, α-amylase, glucoamylase or amylglucosidase, cellulose, dextranase, invertase and α- and β-glucosidase.

These carbohydrases are measured according to conventional methods, and their activities are indicated in units in accordance with the recommendations of the International Union of Biochemistry (Report of the Commission on Enzymes of the IUB, Pergamon Press, Oxford, 1961). The amount by weight of additional enzymes may range from about 1 to about 8 times the amount of glucose oxidase present. Preferably, amyloglucosidase is applied as a carbohydrase.

A dentifrice prepared in accordance with the present invention includes as its essential active ingredient an amount, based upon the dentifrice, of glucose oxidase which forms hydrogen peroxide by oxidative decomposition of its substrate glucose, effective, when applied to a dental surface, to product an approximately neutral range of pH at said dental surface, together with a pharmaceutically acceptable carrier. The approximately neutral pH range will be between about 6 and about 8.

The amount of glucose oxidase can be varied considerably so as to allow for the time needed for the enzyme to dissolve in the saliva, particularly if the dentifrice is in the form of tablets or chewing gum. Preferably, the effective amount of glucose-oxidase will be between about 0.5 and about 20 units per gram/milliliter of the dentifrice, said unit being defined as set forth previously.

The dentifrice of the invention is applied to a dental surface for the purpose of cleaning the surface and suppressing the formation of dental plaque thereon, employing a quantity of dentifrice sufficient to provide the effective quantity of enzyme referred to above, or the unit dosage range of 0.5 to 20 units previously described.

The following tests relate to glucose oxidase, amylglucosidase, and a combination of these components.

In order to show the surprising effect of the enzymes according to the invention the pH-value was measured at the surface of the tooth in the plaque. The microantimony electrode used for this purpose has been described in the literature by F. Clarence Thompson, et al. in the Journal of Dental Research, 33 849 (1954).

The measurements were performed on the buccal surfaces of the first and second molar, at least one hour after the last consumption of food. Thus, there were 4 measuring points in total person, always in the sequence: $M_1SD-M_2SD-M_1SS-M_2SS$.

The tests were performed on groups of 15-30 children (boys and girls) of from 12 to 14 years. The children were divided into 3 groups:
a. those with a pH higher than 6.8
b. those with a pH between 5.6 and 6.8
c. those with a pH lower than 5.6.

The results of the pH measurements are given in the following table:

Table I

| | Percentage of children with pH | | |
|---|---|---|---|
| | 6.8 | 5.6 - 6.8 | 5.6 |
| Controls | | | |
| 1st day | 23 | 53 | 24 |
| 2nd day | 19 | 58 | 23 |
| 30 U amyloglucosidase per 10 ml | | | |
| 1st day | 33 | 39 | 28 |
| 2nd day | 28 | 47 | 25 |
| 6 U glucoseoxidase per 10 ml | | | |
| 1st day | 25 | 55 | 20 |
| 2nd day | 31 | 60 | 9 |
| 30 U amyloglucosidase + 6 U glucoseoxidase per 10 ml | | | |
| 1st day | 21 | 59 | 20 |
| 2nd day | 60 | 40 | 0 |

On the first day the subjects tested rinsed their mouths for 4 minutes with 10 ml of a 70% saccharose solution, after which the pH was measured. After these measurements they rinsed with 10 ml of mouth wash in which the enzymes had been dissolved, which, of course, was not done by the controls. The tests were performed so that there was an interval of at least 1 hour between the last rinse and the next meal.

On the second day the process was repeated with 10 ml of a 70% saccharose solution, after which the pH was measured.

The next day the useful effect of the rinse with enyzme on the pH could be clearly demonstrated by measuring the pH at the surface of the tooth after the rinse with saccharose.

In order to avoid mechanical effect of the plaque both the saccharose and the enzymes were applied in a liquid form.

From the above Table it appears that the hydrolase enzyme amyloglucosidase, by itself, has no appreciable influence on the percentage of children in the danzer zone below pH 5.6, and that glucoseoxidase, and to an even high degree glucose-oxidase in combination with amyloglucosidase, reduces this percentage considerably (23% to 9%) or even to zero.

Another striking factor was that the structure of the plaque had become less firm by the treatment with the enzyme mixture so that the plaque came off easily in many cases.

In the foregoing test using a mouth wash, a reduction of dental surface pH was observed using an oxidoreductase system.

In order to ascertain whether a similar improvement could be obtained employing a toothpaste, comparative tests were performed, as between two toothpastes according to the present invention, namely A and B, a commercial peroxide-containing toothpaste C, and a "blank" toothpaste D containing neither a peroxide nor a peroxide-yielding substrate. Toothpaste A contained glucose oxidase and toothpaste B contained glucose oxidase and amyloglucosidase.

Toothpaste A, B and D had the following identical composition, except for ingredient X:

| Ingredient | % by weight |
|---|---|
| Levilite[x] | 23.0 |
| Methylcellulose | 1.3 |
| Glycerol | 10.0 |
| Sorbitol (70% solution) | 10.0 |
| Sodium benzoate | 0.1 |
| Ethyl-p-hydroxybenzoate | 0.1 |
| Propyl-p-hydroxybenzoate | 0.1 |
| Sodium saccharin | 0.15 |
| Flavor | 0.5 |
| Ingredient X | — |
| Distilled water | to 100% |

[x] a brand of silicon dioxide made by Givaudan Co.

In toothpaste A, ingredient X is 1.2 units of glucose oxidase. In toothpaste B, ingredient X is 1.2 units of glucose oxidase and 15 units amyloglucosidase. In toothpaste D, ingredient X is absent.

Toothpaste C was a commercial toothpaste having the approximate composition:

| Ingredient | % by weight |
|---|---|
| Calcium carbonate | 36 |
| Glycerol | 30 |
| Chloroform | 3.5 |
| Sodium lauryl sulfate | 1.0 |
| Natural tragacanth gum | 1.0 |
| Flavor (peppermint) | 1.0 |
| Peroxide | 0.5 |
| Distilled water | to 100% |

The measurements on the test subjects were performed by the same team consisting of a dental surgeon, a dental assistant, and an administrative assistant. Neither of the first two knew which toothpaste the subject group was using.

Immediately after the first measurement of the dental surface pH, a toffee type of sweet consisting mainly of saccharose was eaten, and exactly 12 minutes later the dental surface pH was measured again. The shifts in pH following the use of the various toothpastes, before and after the use of the sugar, are shown in the following table:

Table II

| Toothpaste | Start pH | pH-shift |
|---|---|---|
| A | 6.28 | +0.47 (before sugar) |
|   | 5.92 | +0.32 (after sugar) |
| B | 6.28 | +0.48 |
|   | 5.80 | +0.55 |
| C | 6.36 | −0.08 |
|   | 6.07 | +0.10 |
| D | 6.51 | +0.20 |
|   | 6.46 | −0.40 |

From the above Table is appears that the toothpastes A and B of the present invention gave a significant rise in pH, whereas the commercial peroxide-containing toothpaste C did not give any statistically significant effect and the blank toothpaste D gave a decrease of the dental surface pH. The only ingredient influencing the pH in the above toothpastes was the calcium carbonate present in toothpaste C. This alkaline component tends to raise the pH, thus masking the unfavorable low dental surface pH actually produced by this toothpaste, which would have been even lower, and hence still more unfavorable, had this polishing agent been replaced by a neutral polishing agent, such as Levilite. But even without taking this factor into account, the differences between the pH shifts caused by the toothpastes according to the invention and the commercial peroxide-containing toothpaste are substantial.

The dentifrices according to the invention can be prepared in various forms, e.g. in the form of toothpaste, mouth wash, tablets, chewing gum or other conventional forms. Besides the enzyme products according to the invention and a substrate, if any, for the oxidase applied these dentifrices contain the conventional ingredients. Thus, for example, these are incorporated in toothpaste abrasive and/or polishing materials such as calcium carbonate, dicalcium phosphate, calcium phosphate, calcium sulphate, or silicon compounds, thickeners such as carboxymethylcellulose, tragacanth or guar, water, flavorings, and/or natural or synthetic sweetening agents. Further, fluoro compounds can be added such as sodium or potassium-monofluoro phosphate or sodium fluoride, and/or thiocyanates.

The dentifrice compositions of the invention are illustrated further by the following examples, to which it is, of course, not limited:

Example I

| Toothpaste | | |
|---|---|---|
| Ingredient | % by weight | |
| Precipitated silica (e.g. Naosyl) | about | 23 |
| Paraffin | | 15 |
| p-Amino benzoic acid (PAB) esters | | 0.2 |
| Methylcellulose | | 1.8 |
| Aromatic substances | | 2 |
| Glucoseoxidase (2.0 U/g) | | |
| Amyloglucosidase (15 U/g) | | |
| Distilled water | | up to 100 |

EXAMPLE II

| Toothpaste | |
|---|---|
| Ingredient | % by weight |
| Calcium carbonate | 50 |
| Tricalcium phosphate | 5 |
| Sorbitol (70% solution) | 10 |
| Glycerol | 20 |
| Tragacanth | 2 |
| Aromatic substances | 0.8 |
| Glucoseoxidase (0.5 U/g) | |
| Dextranase (4 U/g) | |
| p-Amino benzoic acid | |
| PAB-esters | 0.9 |
| Distilled water | up to 100 |

EXAMPLE III

| Toothpaste | |
|---|---|
| Ingredient | % by weight |
| Aluminum-hydroxide | 40 |
| Na-fluoride | 0.1 |
| Sorbitol (70% solution) | 25 |
| Glycerol | 5 |
| Aromatic substances | 1.2 |
| Na-alginate | 1 |
| p-Amino benzoic acid | |
| (PAB)-esters | 0.1 |
| Saccharine | 0.25 |
| Glucoseoxidase (5 U/g) | |
| Water | up to 100 |

EXAMPLE IV

Tooth Powder

| Ingredient | % by weight |
|---|---|
| Aromatic substances | 2 |
| Na-cyclamate | 0.5 |
| Detergent | 1 |
| Glucoseoxidase (1.0 U/g) | |
| Invertase (2.5 U/g) | |
| Calcium phosphate | up to 100 |

EXAMPLE V

Mouth Wash

| Ingredient | % by weight |
|---|---|
| Methylcellulose (low viscous) | 1 |
| Aromatic substances | 1 |
| p-Amino benzoic acid (PAB)-esters | 0.15 |
| Disodium phosphate 0 aq. | 1.5 |
| Citric acid 1 aq. | 1.0 |
| Glucoseoxidase (3 U/ml) | |
| Amyloglucosidase (5 U/ml) | |
| Distilled water | up to 100 |

EXAMPLE VI

Toothpaste

| Ingredient | % by weight |
|---|---|
| Aluminum hydroxide | 35 |
| Precipitated silica | 5 |
| Glycero | 25 |
| Carraghenate | 2 |
| Na-fluoride | 0.1 |
| Detergents | 2 |
| Aromatic substances | 1 |
| K-thiocyanate | 0.02 |
| Glucose oxidase (2.4 U/g) | |
| Water | up to 100 |

EXAMPLE VII

Chewing Tablet

| Ingredient | % by weight |
|---|---|
| Carbowax 6000 | 2 |
| Aromatic substances (micro-capsules) | 0.5 |
| Coloring matter | 0.1 |
| Glucoseoxidase (10 U/g) | |
| Na-fluoride | 0.1 |
| Mannitol | up to 100 |

EXAMPLE VIII

Chewing Gum

| Ingredient | % by weight |
|---|---|
| Gum basis | 14 |
| Sorbitol (70% solution) | 25 |
| Aromatic substances | 0.5 |
| Glucoseoxidase (20 U/g) | |
| Invertase (100 U/g) | |
| Sorbitol | up to 100 |

EXAMPLE IX

Lozenge tablet

| Ingredient | % by weight |
|---|---|
| Calcium gluconate | 57 |
| Mannitol | 40 |
| Aromatic substances | 1 |
| CMC-Na | 2 |
| Glucoseoxidase 20 U/g | |
| Amyloglucosidase 20 U/g | |

What is claimed is:

1. An enzyme dentifrice toothpaste, tooth powder, or mouth wash consisting essentially of about 0.5 to about 20 units per gram/milliliter of glucose oxidase enzyme which forms hydrogen peroxide by oxidative decomposition of a glucose substrate provided by glucose present in sufficient amount in saliva and tooth plaque, said hydrogen peroxide being formed in a continuous concentration no greater than $10^{-4}$%, said unit being the quantity of the enzyme which will oxidize 1 micromol of substrate per minute at 30° C. and pH 6, effective when applied to a dental surface exhibiting a pH below the neutral range, to restore the pH at said dental surface to an approximately neutral range, and a pharmaceutically acceptable carrier.

2. The enzyme dentifrice of claim 1 wherein the concentration of hydrogen peroxide is insufficient to inhibit the saliva enzyme lactoperoxidase required for oxygen transfer from peroxide to oral bacteria cells, and thereby to accomplish bacterial inactivation by hydrogen peroxide, which, if otherwise present in high or moderate concentrations, inhibits the lactoperoxidase, no oxygen transfer to oral bacterial cells takes place, and no oral bacteria inactivation is accomplished.

3. The composition of claim 1 which includes a carbohydrase.

4. The composition of claim 3 in which said carbohydrase is amyloglucosidase.

5. The composition of claim 3 in which the amount by weight of said carbohydrase is from about 1 to about 8 times the amount of glucose hydrase.

6. The method of cleaning a dental surface and suppressing the formation of dental plaque thereon which comprises applying to said dental surface an enzymatic dentifrice, according to claim 2.

7. The method of cleaning a dental surface and suppressing the formation of dental plaque thereon which comprises applying to said dental surface an enzymatic dentifrice according to claim 1.

* * * * *